US010960029B2

(12) United States Patent
Cox, Jr. et al.

(10) Patent No.: US 10,960,029 B2
(45) Date of Patent: Mar. 30, 2021

(54) DEVICES AND METHODS FOR UMBILICAL CORD PROCESSING

(71) Applicant: The Board of Regents of the University of Texas System, Austin, TX (US)

(72) Inventors: Charles S. Cox, Jr., Houston, TX (US); Brijesh S. Gill, Houston, TX (US); Kevin Aroom, Houston, TX (US); Tushar Sharma, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 931 days.

(21) Appl. No.: 15/449,085

(22) Filed: Mar. 3, 2017

(65) Prior Publication Data

US 2017/0252380 A1  Sep. 7, 2017

Related U.S. Application Data

(60) Provisional application No. 62/303,817, filed on Mar. 4, 2016.

(51) Int. Cl.
| *A61K 35/51* | (2015.01) |
| *A61B 17/12* | (2006.01) |
| *A61F 2/46* | (2006.01) |
| *B26B 3/00* | (2006.01) |
| *B26D 1/06* | (2006.01) |
| *B30B 9/20* | (2006.01) |

(Continued)

(52) U.S. Cl.
CPC .............. *A61K 35/51* (2013.01); *A61B 17/12* (2013.01); *A61F 2/46* (2013.01); *B26B 3/00* (2013.01); *B26D 1/06* (2013.01); *B30B 9/20* (2013.01); *C12N 5/0605* (2013.01); *A61B 5/150038* (2013.01); *A61F 2002/4648* (2013.01); *A61M 2202/0462* (2013.01); *A61M 2210/1466* (2013.01)

(58) Field of Classification Search
CPC .......... A61K 35/51; A61B 17/12; A61F 2/46; B26B 3/00; B26D 1/06; B30B 9/20; C12N 5/06

See application file for complete search history.

(56) References Cited

U.S. PATENT DOCUMENTS

| 1,275,414 A | 8/1918 | Forbes |
| 5,000,419 A | 3/1991 | Palmer et al. |

(Continued)

FOREIGN PATENT DOCUMENTS

| WO | WO/2008/060037 | 5/2008 |
| WO | WO/2011/101834 | 8/2011 |

OTHER PUBLICATIONS

Supplementary Partial European Search Report issued in European Application No. 17760900.5, dated Sep. 30, 2019.

(Continued)

*Primary Examiner* — Michele M Kidwell
*Assistant Examiner* — Ilya Y Treyger
(74) *Attorney, Agent, or Firm* — Parker Highlander PLLC

(57) ABSTRACT

Devices and methods for extraction and processing of substantia gelatinea funiculi umbilicalis (Wharton's Jelly) from an umbilical cord. Isolated pluripotent cell compositions and methods of using the same are also provided.

11 Claims, 18 Drawing Sheets

(51) Int. Cl.
*C12N 5/073* (2010.01)
*A61B 5/15* (2006.01)

(56) References Cited

U.S. PATENT DOCUMENTS

| | | | |
|---|---|---|---|
| 5,690,646 | A | 11/1997 | Gruenberg |
| 5,919,702 | A | 7/1999 | Purchio et al. |
| 7,309,055 | B1 | 12/2007 | Spiegel et al. |
| 8,893,995 | B2 * | 11/2014 | Taghizadeh ............ C12M 45/22 241/69 |
| 8,900,863 | B2 | 12/2014 | Kallis et al. |
| 9,012,222 | B2 | 4/2015 | Taghizadeh |
| 2001/0054429 | A1 | 12/2001 | Witter |
| 2005/0197596 | A1 | 9/2005 | Bellucci et al. |
| 2008/0082060 | A1 | 4/2008 | Ogata et al. |
| 2008/0118477 | A1 | 5/2008 | Christopherson |
| 2009/0120957 | A1 | 5/2009 | Phillips |
| 2011/0151556 | A1 | 6/2011 | Kallis et al. |
| 2013/0072951 | A1 | 3/2013 | Trezza et al. |
| 2013/0183273 | A1 | 7/2013 | Taghizadeh |
| 2014/0120615 | A1 | 5/2014 | Fong et al. |

OTHER PUBLICATIONS

Chang, Zhengqi, et al. "Umbilical cord wharton's jelly repeated culture system: a new device and method for obtaining abundant mesenchymal stem cells for bone tissue engineering." *PloS one* 9.10 (2014): e110764.

Hou, Tianyong, et al. "Umbilical cord Wharton's Jelly: a new potential cell source of mesenchymal stromal cells for bone tissue engineering." *Tissue Engineering Part A* 15.9 (2009): 2325-2334.

Hu, Ying, et al. "Wharton's jelly mesenchymal stem cells differentiate into retinal progenitor cells," *Neural regeneration research* 8.19 (2013): 1783.

International Search Report and Written Opinion issued in International Application No. PCT/US2017/020664, dated Jul. 19, 2017.

Kamolz, Lars-Peter, Maike Keck, and Cornelia Kasper. "Wharton's jelly mesenchymal stem cells promote wound healing and tissue regeneration." *Stem cell research & therapy* 5.3 (2014): 62.

Kim, Dae-Won, et al. "Wharton's jelly-derived mesenchymal stem cells: phenotypic characterization and optimizing their therapeutic potential for clinical applications." *International journal of molecular sciences* 14.6 (2013): 11692-11712.

Leeb, Christian, et al. "Promising new sources for pluripotent stem cells." *Stem Cell Reviews and Reports* 6.1 (2010): 15-26.

Lu, Lu-Lu, et al. "Isolation and characterization of human umbilical cord mesenchymal stem cells with hematopoiesis-supportive function and other potentials." *haematologica* 91.8 (2006): 1017-1026.

Montanucci, Pia, et al. "New simple and rapid method for purification of mesenchymal stem cells from the human umbilical cord Wharton jelly." *Tissue Engineering Part A* 17.21-22 (2011): 2651-2661.

Ribeiro, Jorge, et al. "Perspectives of employing mesenchymal stem cells from the Wharton's jelly of the umbilical cord for peripheral nerve repair." *Int Rev Neurobiol* 108 (2013): 79-120.

Taghizadeh, R. R., K. J. Cetrulo, and C. L. Cetrulo. "Wharton's Jelly stem cells: future clinical applications." *Placenta* 32 (2011): S311-S315.

Zhao, Guifang, et al. "Large-scale expansion of Wharton's jelly-derived mesenchymal stem cells on gelatin microbeads, with retention of self-renewal and multipotency characteristics and the capacity for enhancing skin wound healing." *Stem cell research & therapy* 6.1 (2015): 38.

* cited by examiner

Sham

WJ Treated

DEVICES AND METHODS FOR UMBILICAL CORD PROCESSING

This application claims the benefit of U.S. Provisional Patent Application No. 62/303,817, filed Mar. 4, 2016, the entirety of which is incorporated herein by reference.

BACKGROUND OF THE INVENTION

I. Field of the Invention

Embodiments of the present disclosure relate to devices, kits and methods for processing umbilical cords, in particular, the extraction of Wharton's Jelly from umbilical cords.

II. Background of the Invention

Cleft lip and cleft palate (CLP) is the most common birth defect in the United States, affecting more than 2,650 children born each year according to the Centers for Disease Control and Prevention. Cleft palate is the gap in the bony region above the front teeth which causes an opening between the mouth and the nasal cavity leading to insufficient support for front teeth and facial development.

The accepted standard treatment for cleft palate is autologous bone grafting, which provides a stable repair but is invasive and can be followed by potential complications of graft exposure and loss. In addition, autologous bone grafting is subject to donor site morbidity including infection, long-term pain and/or nerve damage that lead to the need of additional surgeries. Another strategy based on using biomaterials seeded with bone marrow (BM) stem cells has proven promising, but BM harvest is too invasive to use in CLP repair in newborns. Accordingly, alternative strategies are needed. In this context, substantia gelatinea funiculi umbilicalis (i.e. Wharton's Jelly) represents a natural biomaterial of great potential. Native Wharton's Jelly (nWJ) is the connective tissue of the umbilical cord, and it is composed of a network of proteoglycans and collagen embedded with perinatal stem cells, a bridge between embryonic and adult stem cells without the limitations of either. It is a natural "tissue engineering" construct that provides a scaffold derived from the recipient's own molecules, naturally seeded with the recipient's own stem cells, and is thus immunologically inert. Since nWJ is typically discarded as post-delivery medical waste, its use does not pose ethical concerns and its harvest is completely non-invasive. The inventors of the inventions disclosed herein have shown in an alveolar defect model representative of cleft palate surgery in the rat, that inclusion of nWJ in the alveolar pocket at the time of palate repair enhances bone growth and accelerates healing, proving to be an adjunct of great potential to orofacial cleft repair. The success of this approach would represent a paradigm shift in the treatment of CLP patients, significantly anticipating the timing of surgical correction and reducing or eliminating the need for subsequent bone grafting.

SUMMARY OF THE INVENTION

In a first embodiment, the invention provides an apparatus for processing an umbilical cord, the device comprising a clamping mechanism, configured to clamp an umbilical cord, and an extraction mechanism, wherein the extraction mechanism is configured to engage the umbilical cord, translate along the umbilical cord, increase hydrostatic pressure within the umbilical cord, and extract matter from the umbilical cord. In some aspects, the extraction mechanism is configured to extract substantia gelatinea funiculi umbilicalis (Wharton's Jelly) from the umbilical cord.

In certain aspects, the extraction mechanism comprises rollers configured to compress the umbilical cord. In particular aspects, the extraction mechanism comprises a first housing and a second housing configured to couple together. In other aspects, the extraction mechanism comprises a first end, a second end, and a plurality rollers between the first end and the second end. In further aspects, the plurality of rollers comprises a first pair of corresponding rollers proximal to the first end of the extraction mechanism and a second pair of corresponding rollers proximal to the second end of the extraction mechanism, and the first pair of corresponding rollers are spaced a first distance apart and the second pair of corresponding rollers are spaced a second distance apart, with the first distance being greater than the second distance.

In additional aspects, the apparatus further comprising a third pair of corresponding rollers between the first and second pairs of corresponding rollers, wherein the third pair of corresponding rollers are spaced a third distance apart, with the third distance being greater than the first distance and less than the second distance.

In some aspects, the clamping mechanism comprises a plurality of protrusions configured to grip the umbilical cord. In particular aspects, the clamping mechanism comprises a first housing and a second housing, and the first housing and the second housing are configured to couple together around the umbilical cord.

In certain aspects, the apparatus further comprises a receptacle configured to retain the matter extracted from the umbilical cord. In specific aspects, the receptacle comprises a first opening configured to receive matter extracted from the umbilical cord and a cover configured to be placed over the first opening. In another aspect, the receptacle comprises a plurality of openings sized to prevent an egress of substantia gelatinea funiculi umbilicalis (Wharton's Jelly) stored within the receptacle. In some aspects, the receptacle may comprise a removable sheath.

A further embodiment of the invention provides a method of extracting matter from an umbilical cord, the method comprising clamping the umbilical cord with a clamping mechanism, engaging the umbilical cord with an extraction mechanism, translating the extraction mechanism along the umbilical cord in a direction away from the clamping mechanism, increasing hydrostatic pressure within the umbilical cord, and extracting matter from the umbilical cord. In a particular aspect, the matter extracted from the umbilical cord is substantia gelatinea funiculi umbilicalis (Wharton's Jelly).

In some specific aspects, the clamping mechanism comprises a first housing and a second housing, and clamping the umbilical cord with the clamping mechanism comprises placing the umbilical cord between the first housing and the second housing, and coupling the first housing and the second housing. In further aspects, the clamping mechanism comprises a plurality of protrusions and clamping the umbilical cord with the clamping mechanism comprises penetrating the umbilical cord with the protrusions.

In other aspects, the extraction mechanism comprises a first housing and a second housing, and engaging the umbilical cord with the extraction mechanism comprises placing the umbilical cord between the first housing and the second housing, and coupling the first housing and the second housing. In certain aspects, the extraction mechanism comprises a plurality of rollers and increasing the hydrostatic pressure within the umbilical cord comprises compressing the umbilical cord with the plurality of rollers.

In further aspects of the method, the extraction mechanism comprises a first end and a second end, and the plurality of rollers comprises a first pair of corresponding rollers proximal to the first end of the extraction mechanism and a second pair of corresponding rollers proximal to the second end of the extraction mechanism, and the second pair of corresponding rollers compress the umbilical cord more than the first pair of corresponding rollers compress the umbilical cord. In particular aspects, the extraction mechanism may additionally comprise a third pair of corresponding rollers between the first and second pairs of corresponding rollers, and the third pair of corresponding rollers compress the umbilical cord more than the first pair of corresponding rollers compress the umbilical cord, but less than the second pair of corresponding rollers compress the umbilical cord.

In certain aspects, the method further comprises retaining the matter extracted from the umbilical cord in a receptacle. In some aspects, the receptacle comprises a first opening configured to receive matter extracted from the umbilical cord and a cover configured to be placed over the first opening. In particular aspects, the matter retained with the receptacle is substantia gelatinea funiculi umbilicalis (Wharton's Jelly) and the receptacle comprises a plurality of openings sized to prevent an egress of the substantia gelatinea funiculi umbilicalis (Wharton's Jelly) retained within the receptacle. In further aspects, the receptacle may comprise a removable sheath. In a specific aspect, the method further comprises removing the removable sheath from the receptacle and placing the receptacle in a container with a preservative solution.

In yet a further embodiment, the invention provides an isolated pluripotent cell composition comprising a Wharton's Jelly having substantially intact tissue structural elements produced by a method according to the embodiments and aspects described herein. In some particular aspects, the Wharton's Jelly exhibits a stiffness of between about 0.01 kPa to 10 kPa.

In still yet a further embodiment, there is provided an isolated pluripotent cell composition comprising a Wharton's Jelly having substantially intact tissue structural elements, wherein the Wharton's Jelly is thixotropic and/or exhibits a stiffness of between about 0.01 kPa to 10 kPa.

In further aspects, the Wharton's Jelly exhibits a stiffness of between about 0.02 kPa to 8 kPa. In some specific aspects, the Wharton's Jelly exhibits a stiffness of greater than 0.1, 0.2, 0.3, 0.4, 0.5, 0.6, 0.7, 0.8, 0.9 or 1.0 kPa. In other aspects, the Wharton's Jelly exhibits a stiffness of between about 0.05 kPa to 5 kPa; 0.1 kPa to 5 kPa; or 0.5 kPa to 3 kPa. In certain aspects, the Wharton's Jelly may be thixotropic.

In additional aspects, the cell composition is frozen. In other aspects, the cell composition has been subjected to one freeze/thaw cycle. In particular aspects, the cell composition has been tested and determined to be free of pathogenic bacteria, viruses and/or fungi. In certain aspects, at least about 80% of the pluripotent cells in the Wharton's Jelly are viable cells. In some specific aspects, the isolated pluripotent cell composition further comprises a preservative or stabilizing reagent.

In yet still a further embodiment, the invention provides a method of treating a subject in need thereof comprising administering to the subject an effective amount of a composition according to the embodiments and aspects described herein. In some aspects, the composition is administered by injection. In other aspects, the composition is administered by surgical implantation. In certain aspects, the subject has a tissue deficit and the composition is administered at the site of the deficit. In a specific aspect, the subject has a cleft palate. In another aspect, the subject has a wound. In additional aspects, the cells in the composition are allogenic relative to the subject. In other aspects, the cells in the composition are HLA matched with the subject.

In still a further embodiment, there is provided a method of culturing a pluripotent cell comprising obtaining a frozen composition according to any of the embodiments and aspects described herein, thawing the composition and isolating a pluripotent cell therefrom, and culturing the pluripotent cell under conditions that maintain pluripotency.

Yet a further embodiment of the invention provides a method of providing a differentiated cell comprising obtaining a frozen composition according to any of the embodiments and aspects described herein, thawing the composition and isolating a pluripotent cell therefrom, culturing the pluripotent cell under differentiation conditions to provide a differentiated cell Certain embodiments include an apparatus for processing an umbilical cord, where the apparatus comprises a handle, a tapered rod coupled to the handle, and a blade coupled to the handle. In particular embodiments, the tapered rod is configured for insertion into a lumen of a blood vessel in an umbilical cord. In specific embodiments the blade comprises a cutting edge, and the tapered rod and blade are positioned such that a radial space exists between the tapered rod and the cutting edge of the blade. In some embodiments, the blade cuts the umbilical cord along a length of the umbilical cord when the tapered rod is inserted into the lumen of the blood vessel in the umbilical cord, and the blade does not cut the blood vessel in umbilical cord when the tapered rod is inserted into the lumen of the blood vessel in the umbilical cord.

Certain embodiments include a method of processing an umbilical cord, where the method comprises obtaining an apparatus as disclosed herein (including for example, an apparatus as described in the immediately preceding paragraph). In particular embodiments, the method comprises inserting the tapered rod of the apparatus into a lumen of a blood vessel of an umbilical cord; cutting the umbilical cord along a length of the umbilical cord with the blade of the apparatus; and compressing the blood vessel of the umbilical cord on the tapered rod without cutting the blood vessel of the umbilical cord.

Some embodiments further comprise pulling the umbilical cord along the tapered rod and toward the handle. Specific embodiments further comprise using forceps to pull the umbilical cord along the tapered rod and toward the handle. In certain embodiments, the blood vessel of the umbilical cord is an umbilical vein.

Particular embodiments include an apparatus for processing an umbilical cord, where the apparatus comprises: a base plate; a motor coupled to the base plate; a reciprocating blade coupled to the motor; and a roller coupled to the base plate. In specific embodiments, the roller is configured to maintain tension on an umbilical cord when the umbilical cord is placed between the roller and the baseplate; and the reciprocating blade is configured to cut a patch from the umbilical cord when the blade engages the umbilical cord.

Certain embodiments further comprise a pair of guide rails coupled to the base plate, where the reciprocating blade is configured to move side-to-side between the rails, and where the motor and the reciprocating are configured to be pushed along the guide rails. Particular embodiments further comprise a pair of arms supporting the roller. In some embodiments, the reciprocating blade is coupled to the mounting bar and wherein the reciprocating blade is configured to move side-to-side between the guide rails along the linear bearing. Specific embodiments further comprise vacuum ports in the base plate. Particular embodiments further comprise a clamp configured to retain an end of the umbilical cord when the umbilical cord is placed between the roller and the baseplate.

Certain embodiments include a method of processing an umbilical cord, where the method comprises obtaining an apparatus as disclosed herein (including for example an apparatus as described in the immediately preceding paragraphs). Particular embodiments include inserting an umbilical cord between the base plate and the roller and engaging the reciprocating blade with the umbilical cord to cut a patch from the umbilical cord. In some embodiments of the method, the base plate of the apparatus comprises a pair of guide rails, and engaging the umbilical cord comprises pushing the reciprocating blade along the guide rails. In specific embodiments, the reciprocating blade moves side-to-side between the guide rails.

In certain embodiments, the umbilical cord comprises Wharton's Jelly, amnion and umbilical arteries before processing. In particular embodiments, the patch comprises Wharton's Jelly and amnion, and in specific embodiments, the patch does not comprise umbilical arteries.

Accordingly, the embodiments of the present disclosure provide for devices, kits and methods of processing umbilical cords to extract substantia gelatinea funiculi umbilicalis (i.e. Wharton's Jelly).

Different umbilical cord components or processed aspects may be referred to herein as a "fiber bundle", "patch", "amnion patch", "blood vessels", "gel" or "goo". Explanations and examples of these terms are provided below.

A fiber bundle is primarily composed of several collagen fibers, along with mesenchymal stem cells and few-to-none smooth muscle cells, bound together in a cylindrical format. The majority of the fiber bundle is sourced from a portion of the umbilical cord usually referred to as the 'Wharton's Jelly' or the 'Umbilical cord tissue'. The fiber bundle has a certain thickness or diameter and length that defines the physical and tensile properties of the fiber bundle. The fiber bundle can be easily sutured or glued to the target site.

A patch is primarily composed of collagen fibers, bound together in a sheet format. The patch is defined by its length, width and the thickness, which defines the physical and tensile properties of the patch. The majority of the fiber bundle is sourced from a portion of the umbilical cord usually referred to as the 'Wharton's Jelly' or the 'Umbilical cord tissue'. Patches can be easily sutured or glued to the target site. The patch is a rich source of MSCs as well.

An amnion patch is primarily composed of the epithelial membrane and its constituents. The amnion patch might or might not have collagen fibers from the portion of the umbilical cord usually referred to as Wharton's jelly.

Blood vessels can refer to the umbilical vein or the umbilical arteries. The blood vessels are primarily composed of smooth muscle cells and connective tissue, but can also carry certain or all components of Wharton's Jelly or umbilical cord tissue. Blood vessels are not a significant source of mesenchymal stem cells (unlike other products described here).

Gel or goo refers to Wharton's Jelly or umbilical cord tissue material in shredded, broken or digested form such that it forms a gelatinous consistency. Gel can be delivered to the target site by injection.

Any embodiment discussed with respect to one aspect of the invention applies to other aspects of the invention as well.

The embodiments in the Example section are understood to be embodiments of the invention that are applicable to all aspects of the invention.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

These and other objects, features, and advantages of the invention will become apparent from the detailed description below and the accompanying drawings.

DETAILED DESCRIPTION OF THE INVENTION

A. General Overview of the Invention

Figure 1:
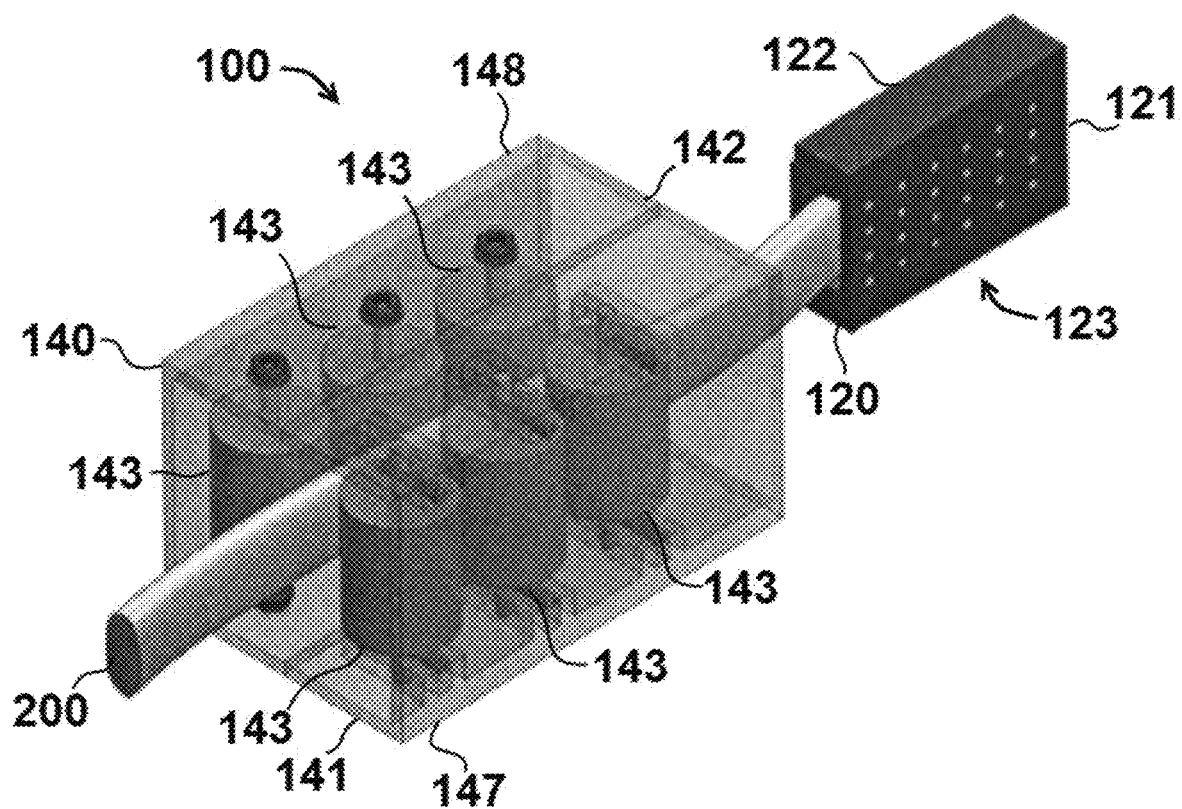
FIG. 1 is a perspective of a first embodiment of an apparatus for processing an umbilical cord.
Figure 2:
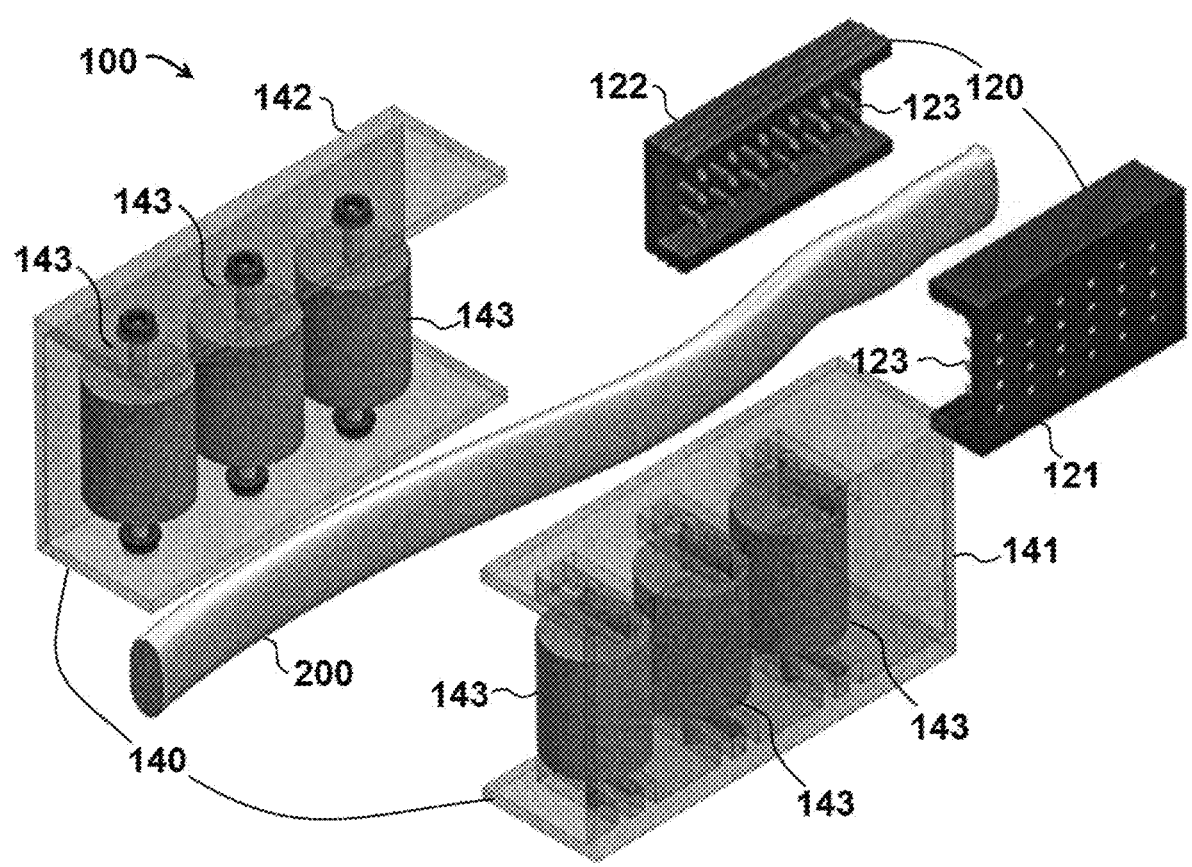
FIG. 2 is an exploded view of the embodiment of FIG. 1.

Referring now to FIG. 1, a perspective view is shown of one embodiment of an apparatus 100 for processing an umbilical cord 200. FIG. 2 provides an exploded view of the embodiment illustrated in FIG. 1. In this embodiment, apparatus 100 comprises a clamping mechanism 120, an extraction mechanism 140, and a receptacle 160. In the illustrated embodiment, clamping mechanism 120 comprises a first housing 121 and a second housing 122 configured to couple together around umbilical cord 200. Housings 121 and 122 further comprise a plurality of protrusions 123 configured to grip umbilical cord 200 when housings 121 and 122 are coupled together around umbilical cord 200.

In the embodiment shown, extraction mechanism 140 comprises a first end 141, a second end 142, as well as a first housing 147 and a second housing 148 configured to couple together. The illustrated embodiment further comprises a plurality of rollers 143 configured to engage and compress umbilical cord 200 in order to increase hydrostatic pressure within umbilical cord 200 as extraction mechanism is translated along umbilical cord 200.

During use, a portion of umbilical cord 200 (e.g. a portion proximal to one end of umbilical cord 200) can be placed between first housing 121 and second housing 122 of clamping mechanism 120. First housing and second housing 122 can then be coupled together such that protrusions 123 engage umbilical cord 200. In certain embodiments, protrusions 123 can be configured as pins or teeth with tapered ends that can penetrate umbilical cord 120 during use. As explained further below, clamping mechanism 120 can secure umbilical cord 200 as extraction mechanism 140 is translated along umbilical cord 200. In particular embodiments, a clamping mechanism may be secured to an umbilical cord at each end of the cord, for example, to assist in straightening a coiled umbilical cord.

A portion of umbilical cord 200 proximal to clamping mechanism 120 can then be placed between first housing 147 and second housing 148 of extraction mechanism 140. First housing 147 and second housing 148 can then be coupled together such that rollers 143 engage umbilical cord 200. The embodiment shown in FIGS. 1 and 2 and described below comprises a single portion of umbilical cord 200 engaged with extraction mechanism 140. It is understood that in other embodiments, umbilical cord 200 may be looped or folded so that two portions of umbilical cord 200 are engaged with extraction mechanism 140. Such a configuration can allow for matter to be extracted from both ends of umbilical cord 200 as extraction mechanism 140 is translated along umbilical cord 200.

In exemplary embodiments, the distance between a roller 143 in first housing 147 and a corresponding roller 143 in second housing 148 is less than the thickness of umbilical cord 200 when first and second housings 147 and 148 are coupled together. Extraction mechanism 140 can then be translated along umbilical cord 200 (e.g. in a direction away from clamping mechanism 120). As extraction mechanism 140 is translated along umbilical cord 200, the hydrostatic pressure within a portion of umbilical cord 200 will be increased as the portion of umbilical cord 200 is engaged by rollers 143.

In certain exemplary embodiments, extraction mechanism 140 may be configured such that the distance between corresponding rollers 143 decreases from first end 141 to second end 142 of extraction mechanism 140. In particular, the distance between rollers 143 proximal to first end 141 can be greater than the distance between rollers 143 proximal to second end 142 (when first housing 147 and second housing 148 are coupled together). In the embodiment shown, for example, rollers 143 proximal to first end 141 will initially increase the hydrostatic pressure within umbilical cord 200, central rollers 143 will further increase the hydrostatic pressure within umbilical cord 200, and rollers 143 proximal to second end 142 will still further increase the hydrostatic pressure within umbilical cord 200. While three sets of corresponding rollers are shown in the extraction mechanism in this embodiment, it is understood that other embodiments may comprise a different number of rollers. In certain embodiments, multiple extraction mechanisms may be provided with different distances between the rollers in each extraction mechanism. Accordingly, each extraction mechanism could be sequentially translated along umbilical cord 200 to increase the hydrostatic pressure within umbilical cord 200. While the embodiment shown comprises three sets of corresponding rollers 143, it is understood that other embodiments may include a different configuration of components to increase hydrostatic pressure within umbilical cord 200. For example, other embodiments may comprise an extraction mechanism including spring-loaded sliding blocks, tapered blocks or other configurations.

As extraction mechanism 140 is translated along umbilical cord 200 and the hydrostatic pressure is increased within umbilical cord 200, matter will be extracted from umbilical cord 200. The increase in the hydrostatic pressure within umbilical cord 200 can allow a user to extract matter from umbilical cord 200. In particular, substantia gelatinea funiculi umbilicalis (also known as Wharton's Jelly) can be extracted for further processing as described below. In certain embodiments, umbilical cord 200 can be scored or sliced prior to translation of extraction mechanism 140 in order to assist in the extraction of Wharton's Jelly. In particular embodiments, extraction mechanism 140 may be used to remove blood from blood vessels. For example, blood can be removed from the vessels using pressure on the blood vessels, moving along the direction of the umbilical cord. Alternatively, centrifugal forces can also be used to remove blood from the blood vessels by spinning the umbilical cord or part at a specified revolutions per minute.

Figure 3:
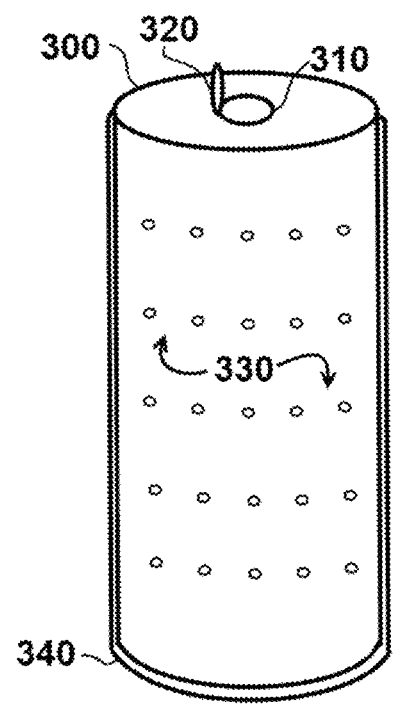
FIG. 3 is a perspective view of a receptacle configured for use with the embodiment of FIG. 1.

Referring now to FIG. 3, certain embodiments can comprise a receptacle 300 for retaining matter extracted from umbilical cord 200. In the embodiment shown, receptacle 300 comprises an opening 310 with a cover 320. Matter extracted from umbilical cord 200 can be directed through opening 310 and into receptacle 300. In a particular embodiment one end of umbilical cord 200 can be placed in opening 310 before extraction mechanism 140 is translated along umbilical cord 200.

After Wharton's Jelly has been placed in receptacle 300, cover 320 can then be placed over opening 310 to prevent contamination of the contents of receptacle 300. In particular embodiments, receptacle 300 may comprise a plurality of openings 330 sized to prevent the egress of Wharton's Jelly. Openings 330 can also be sized to allow the ingress of a preservative solution when receptacle 300 is placed in storage while containing Wharton's Jelly, since the preservative solution is less viscous than the Wharton's Jelly. Receptacle 300 may also comprise a sheath 340 that can prevent contamination of the contents of receptacle 300 through openings 330. In certain embodiments, sheath 340 can be removed from receptacle 300 prior to placing receptacle 300 in storage with a preservative solution.

In particular embodiments, receptacle 300 and sheath 340 are flexible to aid in the extraction process. In addition, receptacle 300 can be configured to maintain its structural integrity at reduced temperatures, including for example −80 degrees Celsius. When desired, receptacle 300 can be removed from the preservative solution and the Wharton's Jelly processed as described below.

Figure 17:
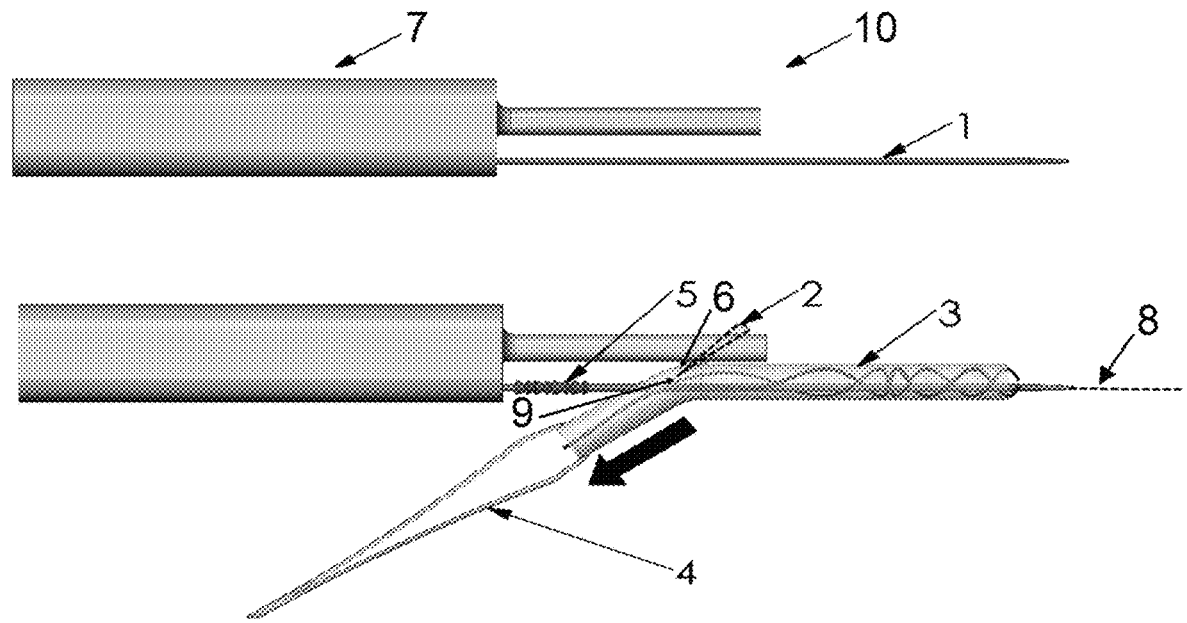
FIG. 17 is a side view of a second embodiment of an apparatus for processing an umbilical cord.
Figure 18:
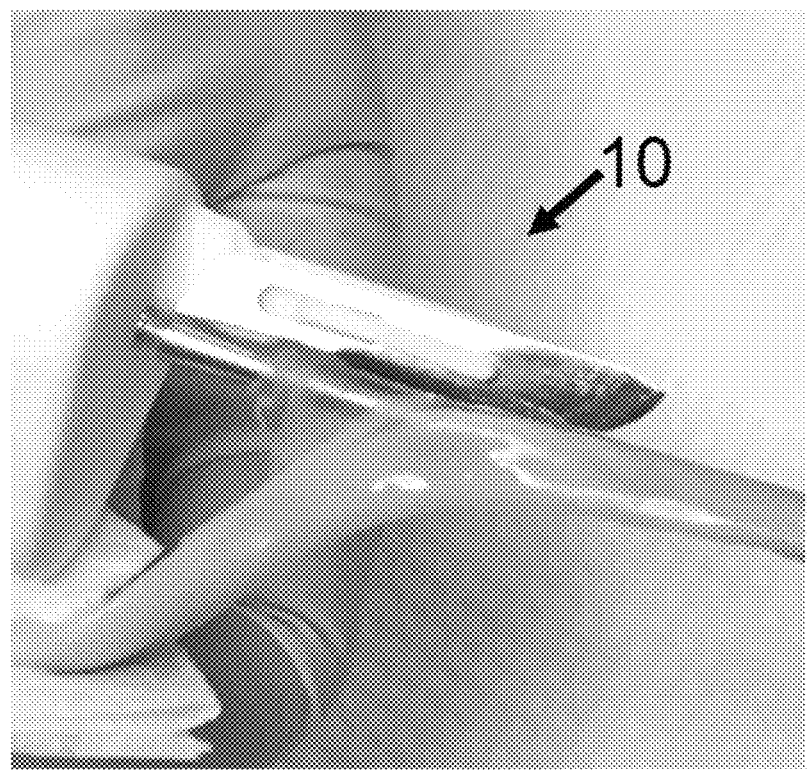
FIGS. 18-20 are photographs of an embodiment of the apparatus of FIG. 17 during use.
Figure 19:
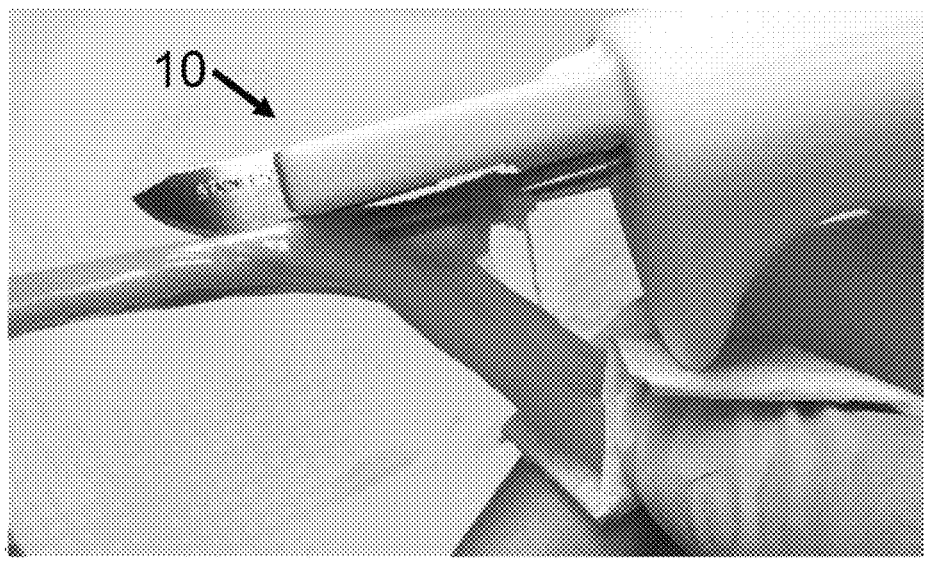
Figure 20:
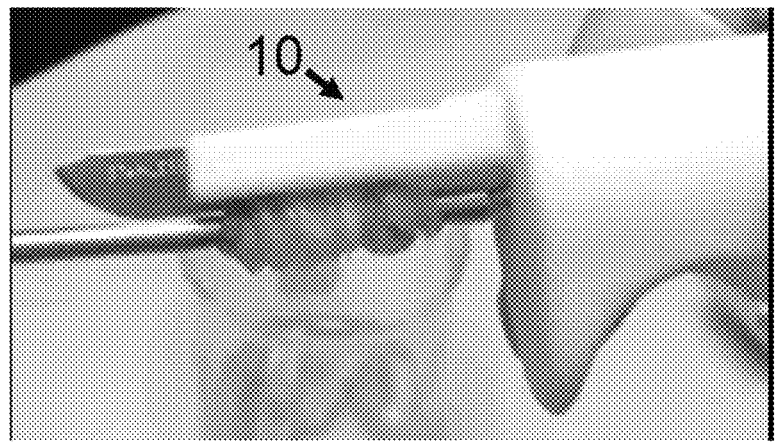

In certain embodiments, a blood vessel harvester can help in removing an umbilical vein from an umbilical cord. In particular embodiments, a blood vessel harvester may comprise a tapered rod or dilator that runs through the blood vessel lumen and a blade that cuts off the excess umbilical cord tissue external to the blood vessel walls. FIG. 17 illustrates a schematic of one such blood vessel harvester device 10, and FIGS. 18-20 include photographs of device 10 in use. The blade used in this embodiment is a surgically sharp and disposable blade, which is coupled to the device a certain distance from the dilator surface. This distance between the dilator and the edge of the blade would be great than the typical thickness of the blood vessel wall.

As illustrated in FIG. 17, umbilical vein removal can be accomplished with the use of a device 10 comprising a handle 7 with a fixed tapered rod 1 and a fixed blade 2. In certain embodiments, the cutting line of blade 2 is aligned with a primary axis 8 of rod 1 (i.e. an axis concentric and parallel with rod 1), with a radial space 9 between cutting edge 6 and rod 1. A properly prepared umbilical cord 3 is mounted by inserting rod 1 into the lumen of umbilical vein 5 of umbilical cord 3. Once the proximal end of umbilical cord 3 is mounted, a portion of umbilical cord 3 other than umbilical vein 7 is grabbed by a hemostat or forceps 4 and pulled further down rod 1 towards blade 2, until blade 2 engages with the outer surface of umbilical cord 3.

At this stage in the harvesting process, a longitudinal slit can be cut on one side of umbilical cord 3. Radial space 9 between cutting edge 6 of blade 2 and the surface of rod 1 prevents umbilical vein 5 from being cut. As the operator pulls on umbilical cord 3, a portion of umbilical vein 5 separates from the other components of umbilical cord 3 (including most of the Wharton's Jelly and umbilical arteries). When the umbilical cord 3 has been fully pulled through, the final result would be a compressed umbilical vein 5 remaining on 1 rod a primarily intact, "butterflied" (e.g. cut along its length) umbilical cord 3.

Figure 21:
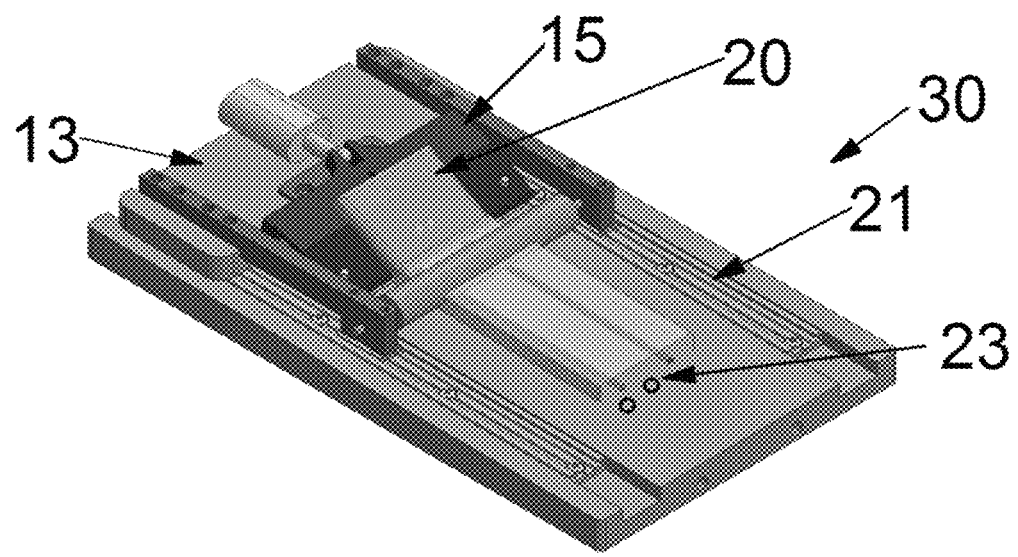
FIG. 21 is a perspective view of a third embodiment of an apparatus for processing an umbilical cord.
Figure 22:
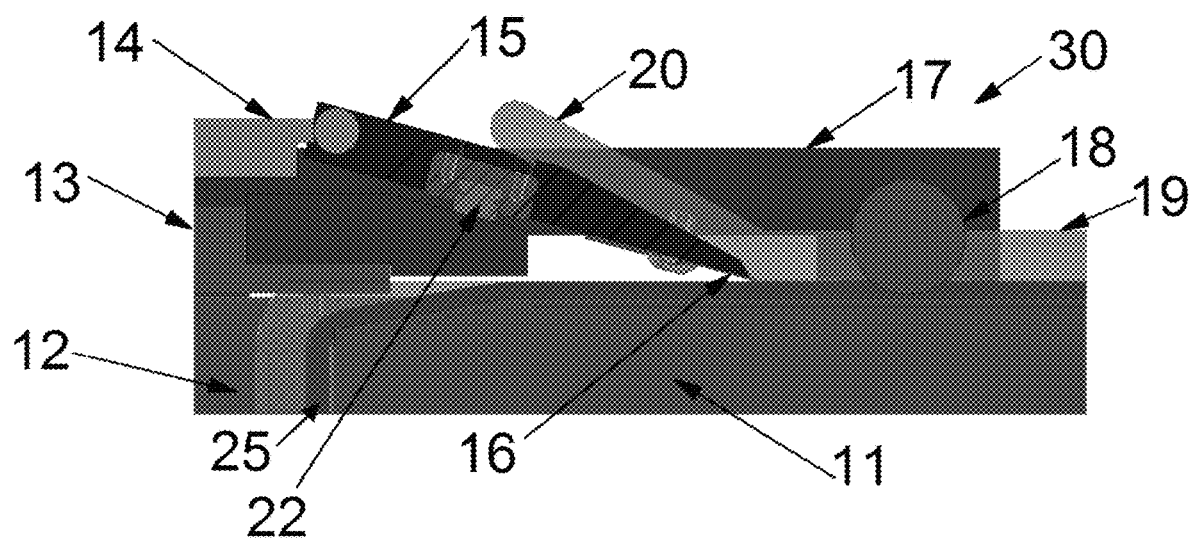
FIG. 22 is a side section view of the embodiment of FIG. 21.

Referring now to FIGS. 21-22, particular embodiments may also include a patch harvester device 30 to assist in obtaining patches from a thick umbilical cord 19 tissue segment. It may be preferable to remove the umbilical vein using blood vessel harvester device 10 and then use patch harvester device 30 in order to obtain a patch comprising primarily Wharton' Jelly. In the embodiment shown, device 30 uses one or more reciprocating blades 16 to slice a sheet or patch of Wharton's Jelly from a butterflied umbilical cord 19 (e.g. an umbilical cord cut along its length). In this embodiment, umbilical cord 19 is arranged on a base plate 11 and a clamp jaw 12 is tightened to compress the proximal end of umbilical cord 19.

In this embodiment, a carriage 13 comprising a motor 14, a blade mounting bar 15, a blade 16, and a linear bearing 22 is inserted into a pair of guide rails 21. In exemplary embodiments motor 14 may be powered by electric power or an air supply. Guide rails 21 maintain a gap between base plate 11 and blade 16. During operation, carriage 13 can be pushed forward (e.g. along guide rails 21) by the operator. In addition, motor 14 can simultaneously drive blade mounting bar 15 and attached blades 16 back and forth (e.g. side-to-side between guide rails 21 and perpendicular to the direction of carriage 13). Distal to blade 16, a pair of arms 17 support a roller 18 that compresses a portion of umbilical cord 19 in preparation for cutting. In this embodiment, roller 18 also maintains tension on umbilical cord 19. During operation base plate 11 clamps on to umbilical cord 19 to avoid undesired movement of the umbilical cord 19 while the patch is being harvested. In certain embodiments, base plate 11 can be made using a soft material or metal, and can have multiple clamps to hold onto various parts of umbilical cord 19. Base plate 11 can also have vacuum hold-down ports 23 or be made out of absorbent material to assist securing the distal part of umbilical cord 19 to avoid unwanted displacement. Additionally, patch harvester device 30 could also be operated in a cold environment so that umbilical cord 19 tissue is more rigid compared to room temperature.

As blade 16 engages with umbilical cord 19, a portion 20 (comprising primarily Wharton's Jelly) is cut and slides on top of blade mounting bar 15. Portion 20 can optionally be grabbed by forceps. During operation, carriage 13 slides along base plate 11, cutting umbilical cord 19 into two separate pieces: portion 20 primarily comprising Wharton's Jelly, and a second portion 25 comprising arteries and amnion.

In preparation for the extraction processes described above, the umbilical cord should be collected, transported and preserved in a sterile environment. At the delivery site, the umbilical cord should be unclamped and suspended in buffered solution containing heparin and an antibiotic (e.g. gentamycin). The umbilical cord should be kept under cold conditions (e.g. approximately 4 degrees Celsius) for short term preservation or transportation to the processing site.

Figure 23:
FIG. 23 is a photograph of tissue samples obtained using the apparatus of FIG. 22.

To process the umbilical cord, the umbilical cord can be removed and washed in buffered solution containing heparin and antibiotic. A roller compression device (including for example a device similar to that shown in FIGS. 1 and 2) can be used to push out blood or clots remaining in the blood vessels. Once the blood has been removed, the vein can be removed using a blood vessel harvester as shown in FIGS. 17-20. After the vein has been removed, the remaining umbilical cord, containing the arteries and Wharton's Jelly, can be placed on a patch harvesting device as shown in FIGS. 21 and 22. The rollers and/or clamps on the patch harvester can be used to lock the umbilical cord in place, and the device can be used to obtain a Wharton's jelly patch, which should remain clamped behind on the device. The shaved off portion of the umbilical cord containing arteries, amnion and some Wharton's Jelly (shown in FIG. 23) can be set aside as a source of mesenchymal stem cells. If required, the arteries can be manually removed by grabbing on to one of its ends and pulling the artery along the length of the shaved off portion.

In certain embodiments, the edges of the patch that remain clamped or that might still have amnion and some of the arteries remaining can be manually cut off. The patch can then be unclamped and the pure Wharton's Jelly patch can be separated from the rest of the umbilical cord tissue. Finally, the Wharton's Jelly Patch can be washed and stored as per cryogenic procedures.

Certain embodiments may also include fiber bundle harvesting procedures. Particular embodiments of fiber bundle harvesting procedures utilize blood vessel removal or amnion tearing. For example, the umbilical cord can be removed and washed in buffered solution containing heparin and antibiotic a few times. A roller compression device (including for example a device similar to that shown in FIGS. 1 and 2) can be used to push out blood or clots remaining in the blood vessels. Once the blood has been removed, the vein can be removed using a blood vessel harvester as shown in FIGS. 17-20. After the vein has been removed, the remaining umbilical cord, containing the arteries and Wharton's Jelly, can be placed on a patch harvesting device as shown in FIGS. 21 and 22. The rollers and/or clamps on the patch harvester can be used to lock the umbilical cord in place, and the device can be used to obtain a Wharton's jelly patch, which should remain clamped behind on the device. The shaved off portion of the umbilical cord containing arteries, amnion and some Wharton's Jelly (shown in FIG. 23) can be set aside as a source of mesenchymal stem cells.

The edges of the patch that remain clamped or that might still have amnion and some of the arteries remaining can be manually cut off. A thin segment of the fiber bundle from the Wharton's Jelly patch area can then be manually cut off. The patch can then be unclamped and the pure Wharton's Jelly patch can be separated from the rest of the umbilical cord tissue. Finally, the Wharton's Jelly Patch can be washed and stored as per cryogenic procedures.

Figure 24:
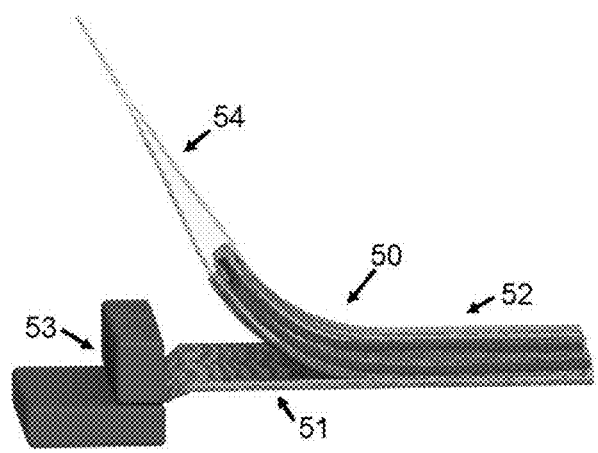
FIG. 24 is a perspective view of a technique for processing an umbilical cord.
Figure 25:
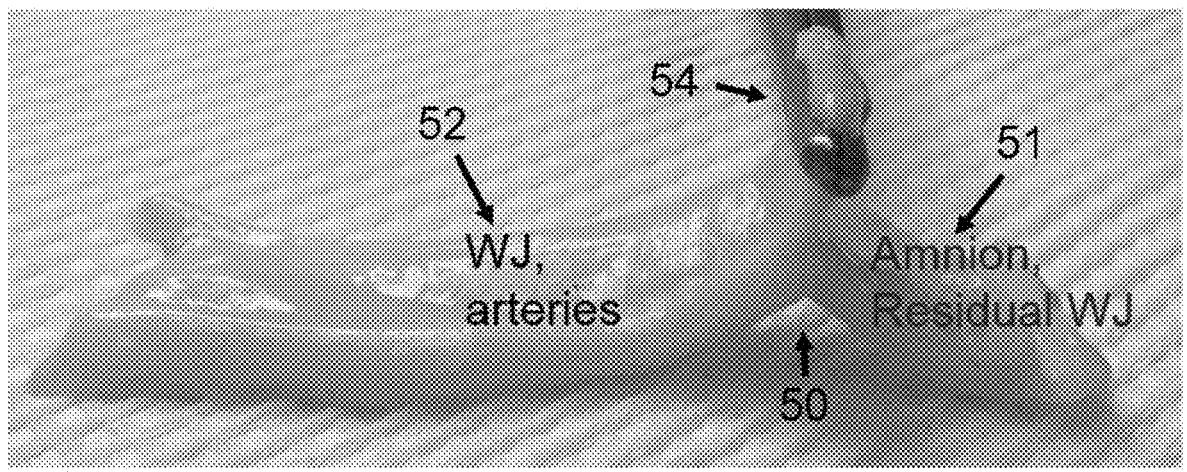
FIG. 25 is a photograph of tissue samples obtained using the technique of FIG. 24.

In certain embodiments fiber bundle harvesting procedures can utilize a grab and pull technique as shown in FIGS. 24 and 25. Wharton's Jelly 50 is composed of fibrous tissue containing primarily collagen, which can be manually pulled to obtain different structures, such as fiber bundles or patches. This embodiment allows one to obtain pure Wharton's Jelly structures without tearing amnion 51 or removal of any blood vessels 52. The grab and pull technique comprises two steps. The first step involves making an incision on one of the ends to free up the tissue that needs to be extracted. The second step includes grabbing on to the free tissue end with a clamp 53 and forceps 54 and pulling it along the length of the umbilical cord.

The umbilical cord tissue 'peels' off the remaining umbilical cord due to the tension applied by the pull. For an intact, the portion of the umbilical cord tissue to be extracted needs to be grabbed on its loose end and then pulled along the umbilical cord length such that the tweezer tips move inside the umbilical cord, along the blood vessels of the UC umbilical cord. This technique works better for umbilical cords where the blood vessels are not coiled or twisted inside the cord.

Figure 26:
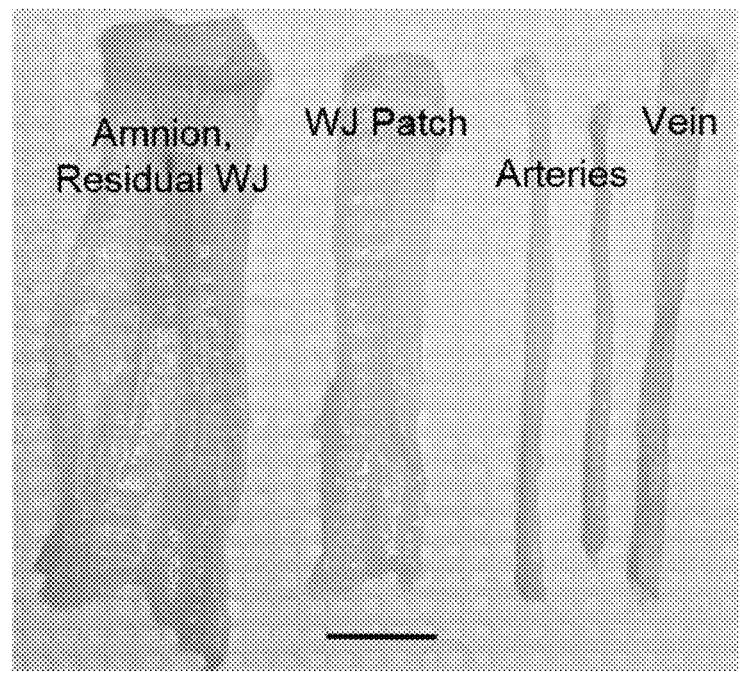
FIGS. 26-27 are photographs of tissue samples and products obtained using the devices and methods disclosed herein.
Figure 27:
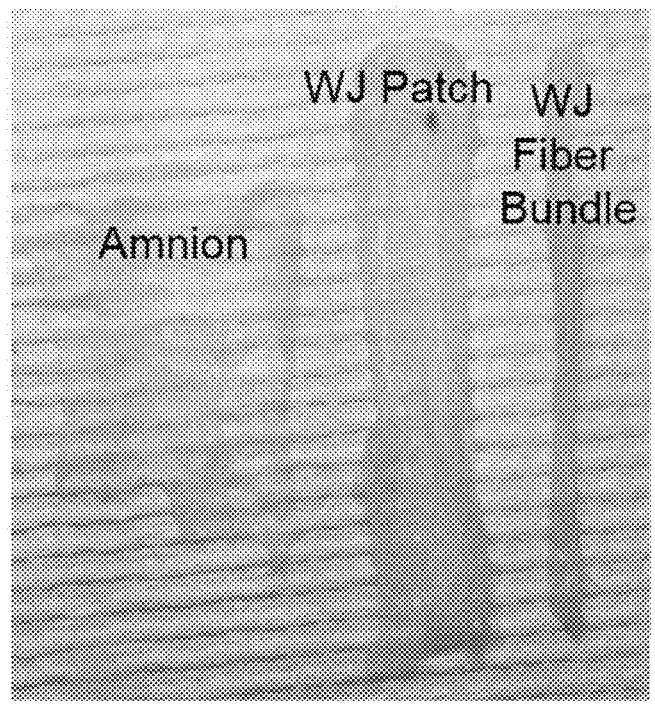

Examples of tissue samples and various products obtained using the devices and methods disclosed herein are shown in FIGS. 26 and 27. These products include amnion, residual Wharton's Jelly, a Wharton's Jelly patch, arteries, and a vein.

B. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A device was designed to provide extraction of Wharton's Jelly compositions from umbilical cord. The device configuration is detailed above and shown in FIGS. 1-3. Importantly, the device allows for the extraction of Wharton's Jelly having substantially intact microstructures, such as veins and arterial tissues, as well extracellular matrix allow the Jelly to remain cohesive.

Figure 4:
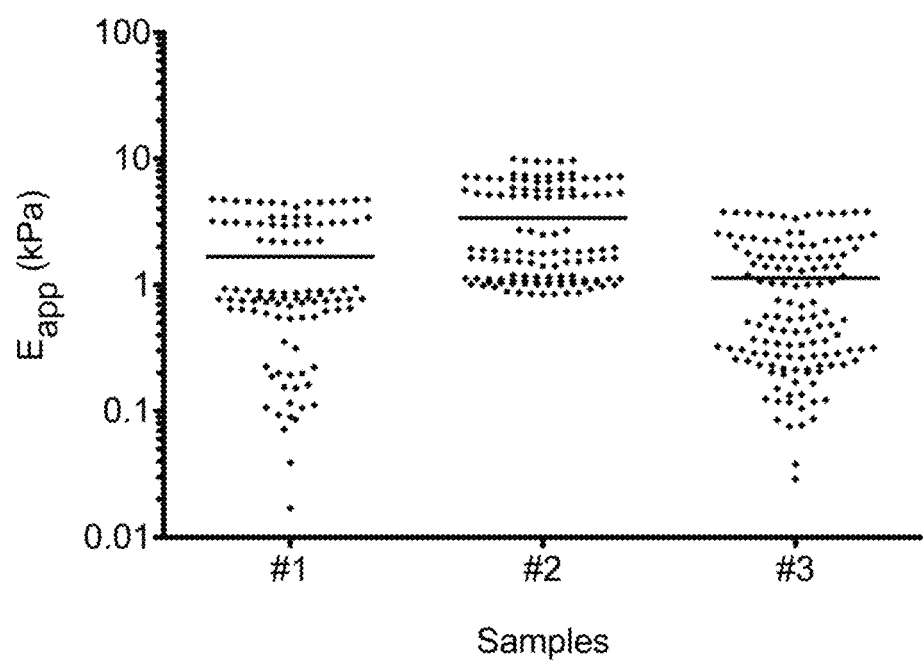
FIG. 4 is a graph showing the results of atomic force microscopy studies to determine the stiffness of samples of Wharton's Jelly. Three sample were tested and exhibited stiffness range of 0.029 kPa-7.61 kPa (similar to other soft tissues found in the body such as brain and liver) and a Young's Modulus of 2.06+/−1.18 kPa.

Next, studies were undertaken to assess the properties of Wharton's Jelly compositions extracted by the instant device and methods. Atomic force microscopy studies were used to determine the stiffness of samples of Wharton's Jelly. Results of these studies are shown in FIG. 4. Three sample were tested and exhibited stiffness range of 0.029 kPa-7.61 kPa (similar to other soft tissues found in the body such as brain and liver) and a Young's Modulus of 2.06+/−1.18 kPa.

Figure 5A:
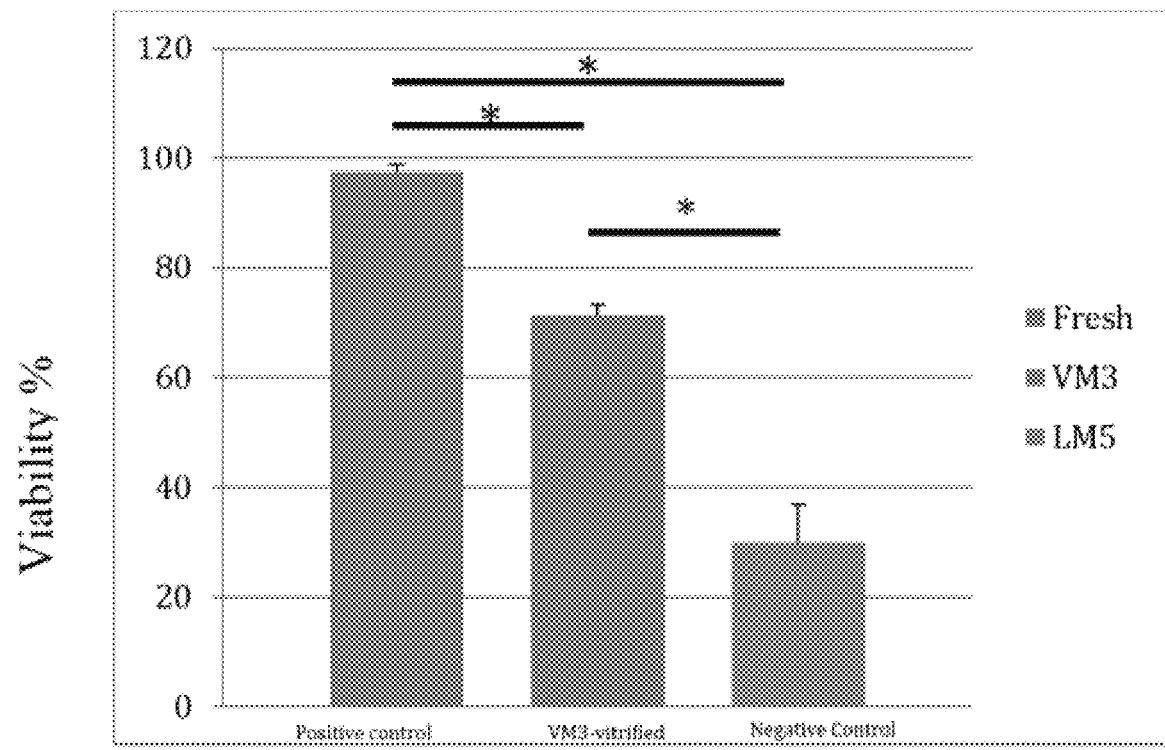
FIG. 5A is a graph showing the effect of vitrification treatment on cell viability in samples of Wharton' Jelly. The results show that maximal cell viability is maintained when the structure of the gel remains intact.
Figure 5B:
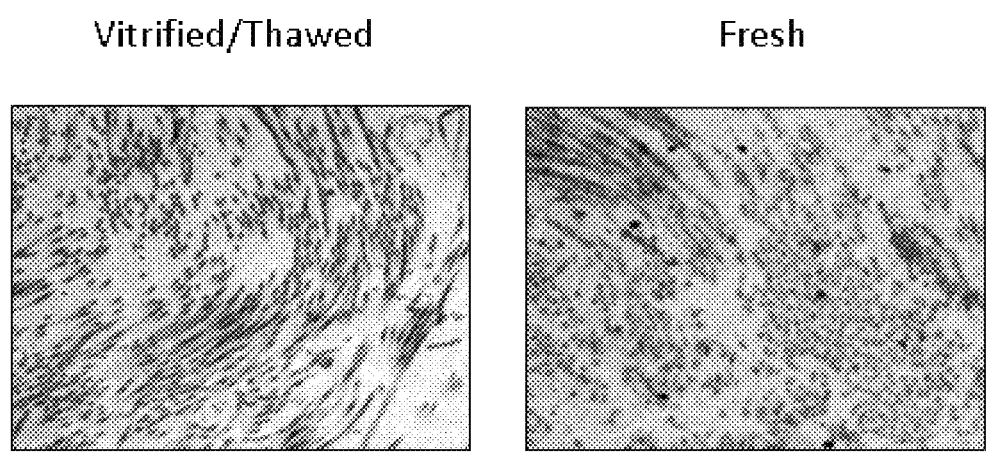
FIG. 5B are images showing microscopic analysis of Wharton's Jelly matrix structure before or after vitrification. Vitrification is shown to substantially the matric structures.

Next, the viability of pluripotent cells in a substantially intact Wharton's Jelly (e.g. extracted by the methods herein) were assess as compared to samples that have been vitrified. Results of these studies are shown in FIG. 5A and demonstrate that maximal cell viability is maintained when the structure of the gel remain intact. Imagining studies presented in FIG. 5B likewise show microscopic analysis of Wharton's Jelly matrix structure before or after vitrification. Vitrification is shown to substantially the matrix structures.

Figure 6:
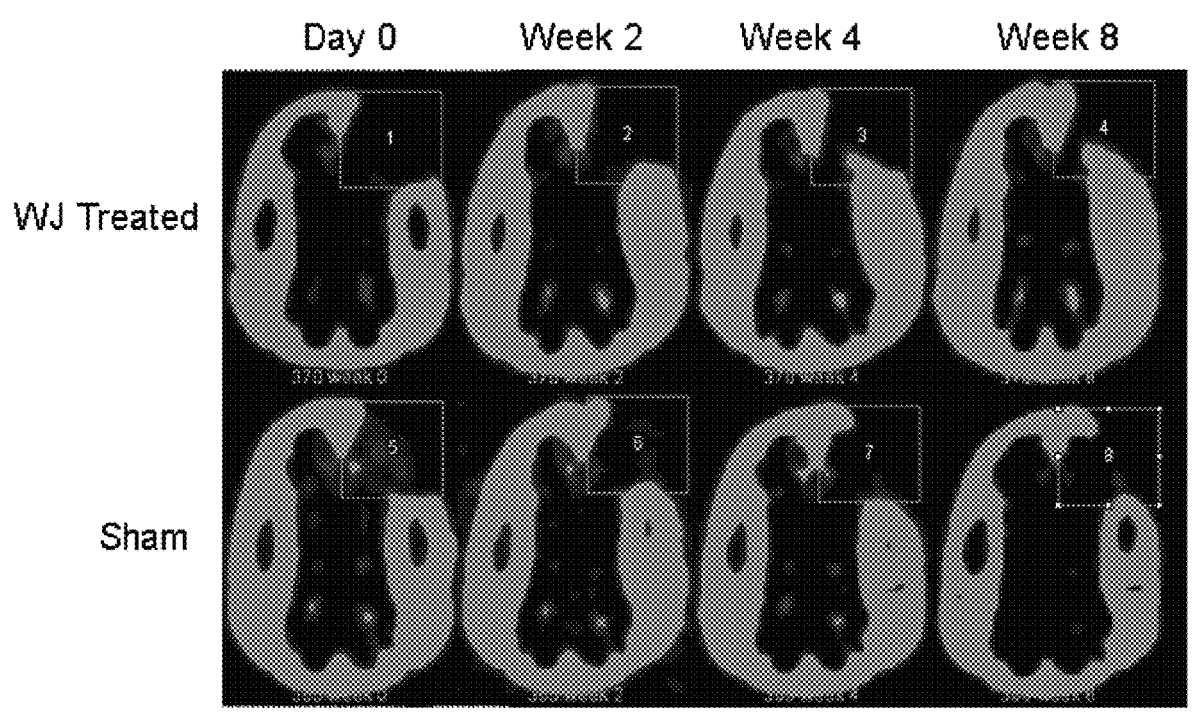
FIG. 6 shows the results of CT imaging in a rat model for a critical size alveolar defect. At day zero the critical defect size was 7×4×3 mm and animals were either treated with implantation of Wharton's Jelly or control ("sham") treatment. Treated animals were monitored for 8 weeks by analysis of bone growth using flat panel CT imaging on the day of surgery (day 0) and at 2, 4 and 8 weeks post-surgery.
Figure 7:
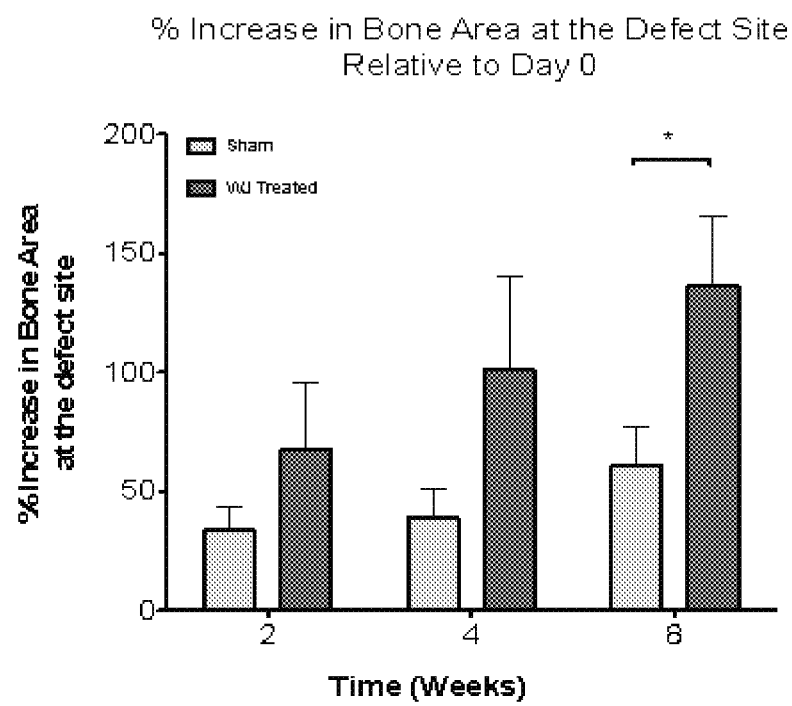
FIG. 7 is a graph showing quantification of new bone formation in Wharton's Jelly or control ("sham") treated rats. The graph shows the percent increase in bone area (relative to day zero) in the deficit site at 2, 4 and 8 weeks post-treatment. The results indicate that treatment with the Wharton's Jelly composition was significantly more effective than the control treatment in increasing bone area.
Figure 8:
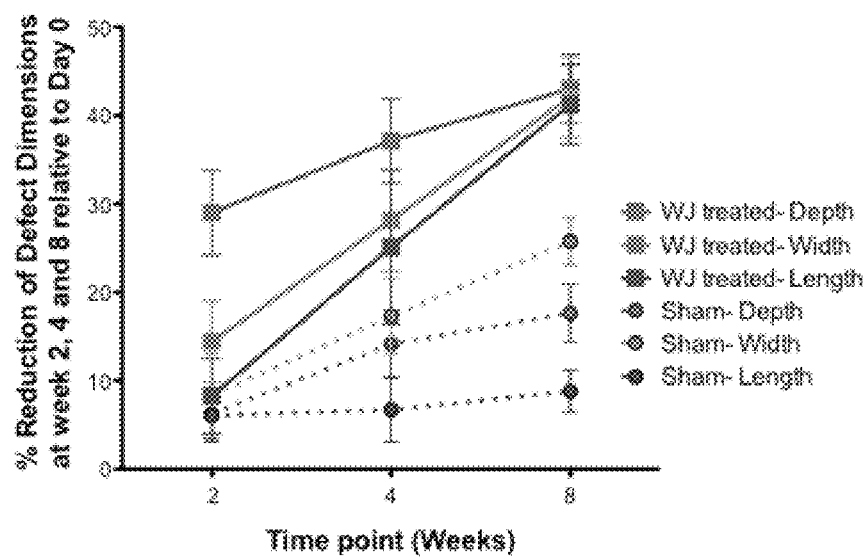
FIG. 8 is a graph showing quantification of new bone formation in Wharton's Jelly or control ("sham") treated rats. The graph shows the percent reduction in the depth, width and length of the deficit site (relative to day zero) at 2, 4 and 8 weeks post-treatment. The results indicate that treatment with the Wharton's Jelly composition was significantly more effective than the control treatment in reducing all dimensions of deficit size.
Figure 9:
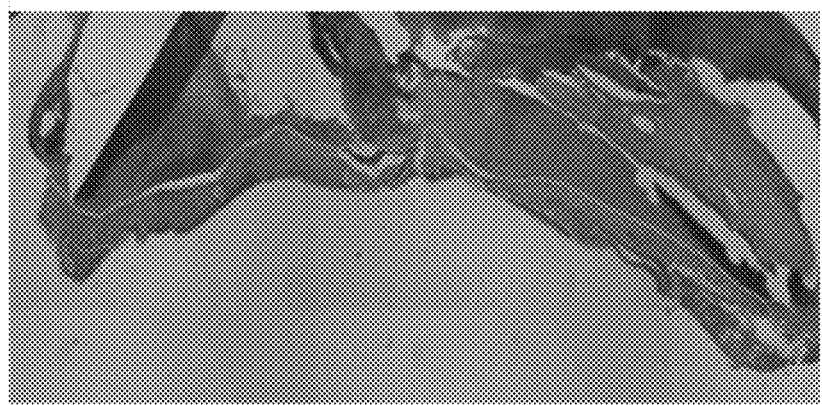
FIG. 9 shows histology analysis of rats treated with Wharton's Jelly or control treatment at 8 weeks post-surgery. Areas of new bone formation are indicated.
Figure 9:
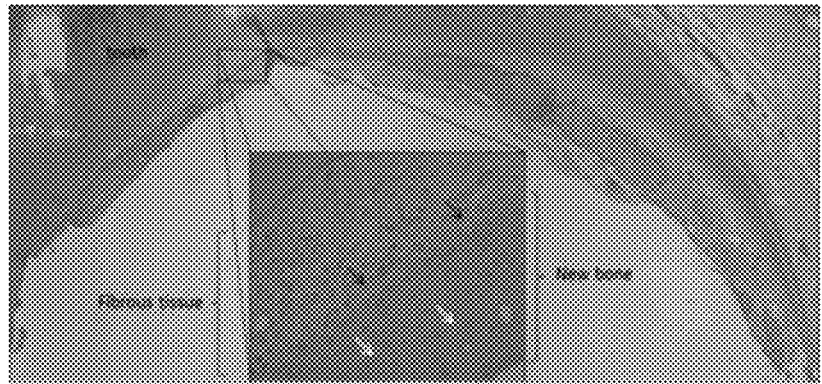
Figure 10:
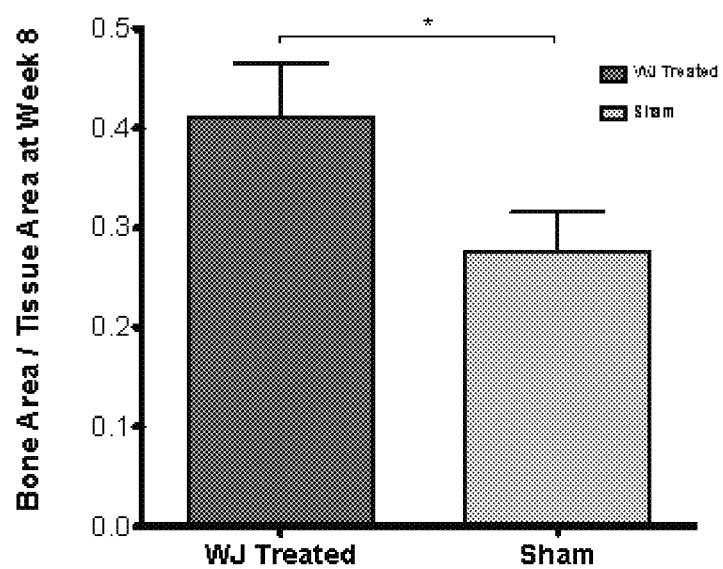
FIG. 10 is a graph of the results of histology analysis of rats treated with Wharton's Jelly or control treatment at 8 weeks post-surgery. The studies demonstrated that the Wharton's Jelly compositions were significantly more effective at generating additional bone tissue in the treated animals.

One of the indications that could potentially be effectively treated with Wharton's Jelly compositions is cleft palate. Accordingly, a rat model system that has a critical size alveolar defect was studies to assess the effectiveness of Wharton's Jelly in filling a tissue deficit. For these studies, animals were either treated with implantation of Wharton's Jelly or control ("sham") treatment. At day zero the critical defect size was 7×4×3 mm. Following treatment animals were monitored for 8 weeks by analysis of bone growth using flat panel CT imaging on the day of surgery (day 0) and at 2, 4 and 8 weeks post-surgery. FIG. 6 shows the results of CT imaging in study animals and demonstrates significant tissue regrowth in animals treated with Wharton's Jelly compositions produced by the methods detailed herein. The results of these studies were also quantified as shown in FIGS. 7-8. The graph in FIG. 7 shows the percent increase in bone area (relative to day zero) in the deficit site at 2, 4 and 8 weeks post-treatment. The results indicate that treatment with the Wharton's Jelly composition was significantly more effective than the control treatment in increasing bone area. The graph in FIG. 8 shows the percent reduction in the depth, width and length of the deficit site (relative to day zero) at 2, 4 and 8 weeks post-treatment. Again, the results indicate that treatment with the Wharton's Jelly composition was significantly more effective than the control treatment in reducing all dimensions of deficit size. FIG. 9 shows histology analysis of rats treated with Wharton's Jelly or control treatment at 8 weeks post-surgery, with areas of new bone formation indicated. The graph in FIG. 10 shows the results of histology analysis of rats treated with Wharton's Jelly or control treatment at 8 weeks post-surgery. The studies further demonstrated that the Wharton's Jelly compositions were significantly more effective at generating additional bone tissue in the treated animals.

Figure 11:
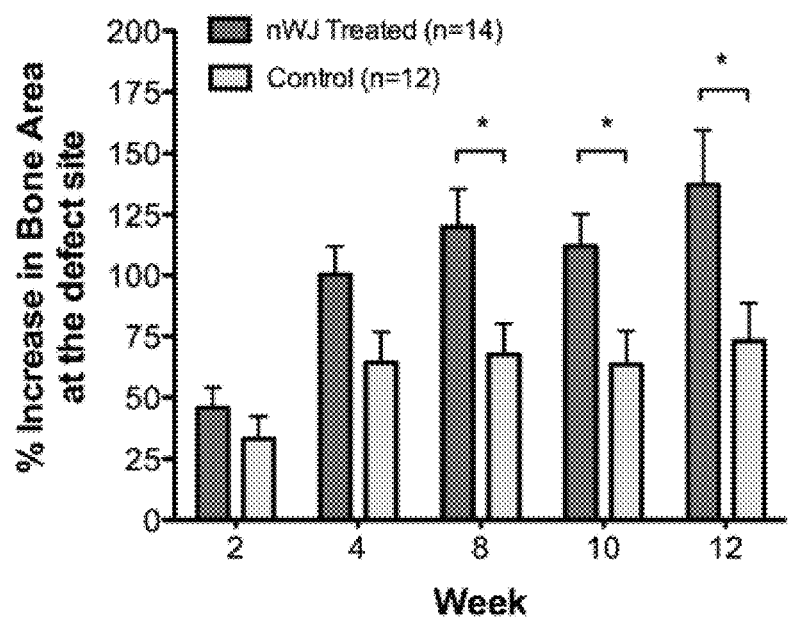
FIG. 11 is a graph showing quantification of new bone formation in Wharton's Jelly or control ("sham") treated rats. The graph shows the percent increase in bone area (relative to day zero) in the deficit site at 2, 4, 8, 10 and 12 weeks post-treatment. The results indicate that treatment with the Wharton's Jelly composition was significantly more effective than the control treatment in increasing bone area. This was especially apparent when the later time points of treatment (e.g., 8, 10 and 12-weeks post treatment) were analyzed.
Figure 12:
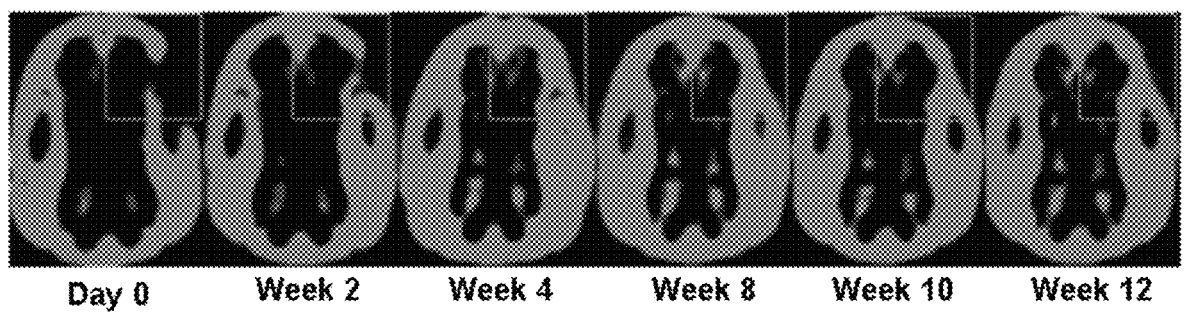
FIG. 12 shows an example result of CT imaging in a rat having critical size alveolar defect that was treated with the Wharton's Jelly composition and exhibited particularly robust response. As shown in the imaging, by week 12 the animal showed nearly complete deficit repair.

To determine the effectiveness of the Wharton's Jelly compositions at later time points, the same studies in the rat model detailed above were repeated but animals were also assessed at 10 and 12 weeks post treatment. Study results in FIG. 11. Here new bone formation is quantified in Wharton's Jelly or control ("sham") treated rats. The graph shows the percent increase in bone area (relative to day zero) in the deficit site at 2, 4, 8, 10 and 12 weeks post-treatment. The results indicate that treatment with the Wharton's Jelly composition was significantly more effective than the control treatment in increasing bone area. This was especially apparent when the later time points of treatment (e.g., 8, 10 and 12-weeks post treatment) were analyzed. In fact, one animal responded particularly well to the treatment. CT imaging of this animal is shown in FIG. 12 and by week 12 the animal showed nearly complete deficit repair.

Figure 13:
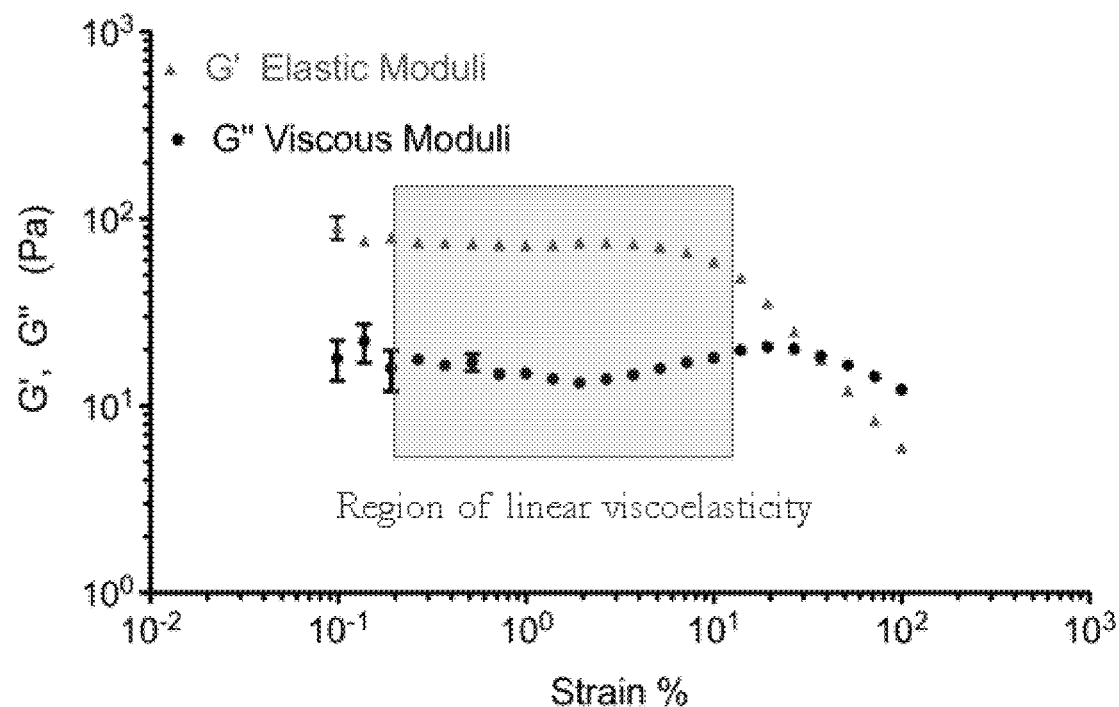
FIG. 13 is a graph showing the results of a strain sweep test to determine the limit of linear viscoelasticity for the Wharton's Jelly compositions.
Figure 14:
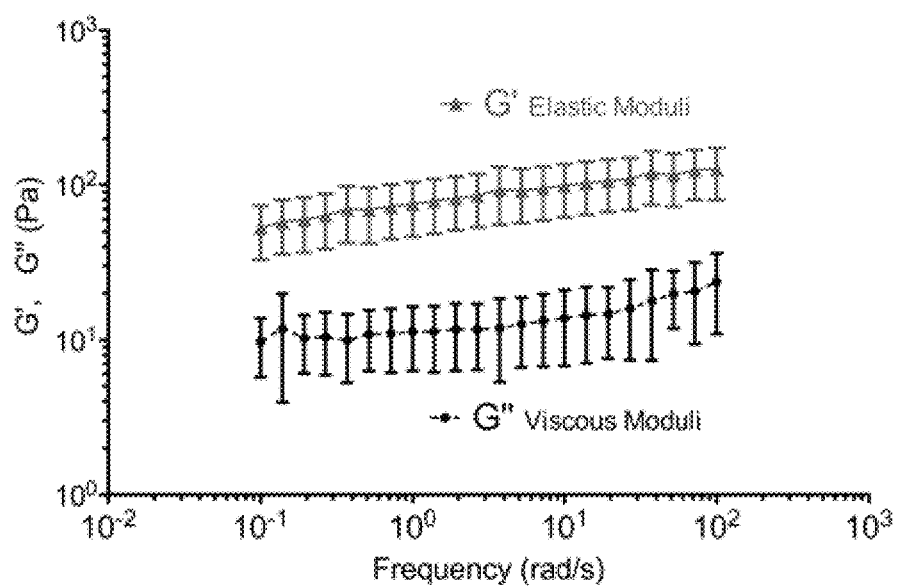
FIG. 14 is a graph showing the results of a dynamic frequency sweep test to assess the structural response to deformations for the Wharton's Jelly compositions. In these studies viscoelastic properties of a sample are determined as a function of timescale. For the tested sample, elastic modulus is dominant over the viscous modulus at all frequencies. As the frequency increased the material appears to stiffen.
Figure 15:
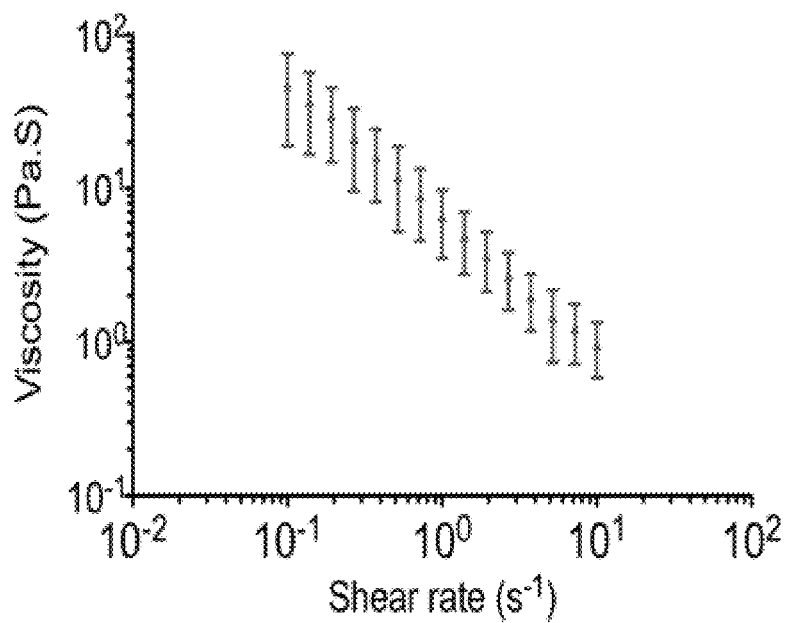
FIG. 15 is a graph showing viscosity profiling for the Wharton's Jelly compositions. Viscosity is not a fixed value but is dependent upon the degree of shear the material is exposed to. The Wharton's Jelly compositions display shear-thinning, a phenomenon where viscosity decreases with increasing applied shear rate.

Next, to gain insight into the behavior of the microstructure of the Wharton's Jelly compositions produced by the methods of the embodiments the compositions were subjected to rheological testing. Specifically, an ARES rheometer was used to perform tests designed to determine: the linear viscoelastic region of Wharton's Jelly; assess the structural response to deformations; and determine viscosity profiling as a function of shear. For the tests Wharton's Jelly compositions are sandwiched between two parallel plates. The lower plate delivers shear of specific frequency range. The upper plate has a piezoelectric force transducer that detects response (shear force) in the test composition. A graph showing the results of a strain sweep test to determine the limit of linear viscoelasticity for the Wharton's Jelly compositions (a measurement of stability of the structures in the sample) is shown in FIG. 13. FIG. 14 is a graph showing the results of a dynamic frequency sweep test to assess the structural response to deformations for the Wharton's Jelly compositions. In these studies, viscoelastic properties of a sample are determined as a function of timescale. For the tested sample, elastic modulus is dominant over the viscous modulus at all frequencies. As the frequency increased the material appears to stiffen. Next the viscosity of the compositions was studied. Viscosity is not a fixed value but is dependent upon the degree of shear the material is exposed to. As shown in FIG. 15, the Wharton's Jelly compositions display shear-thinning, a phenomenon where viscosity decreases with increasing applied shear rate.

Figure 16A:
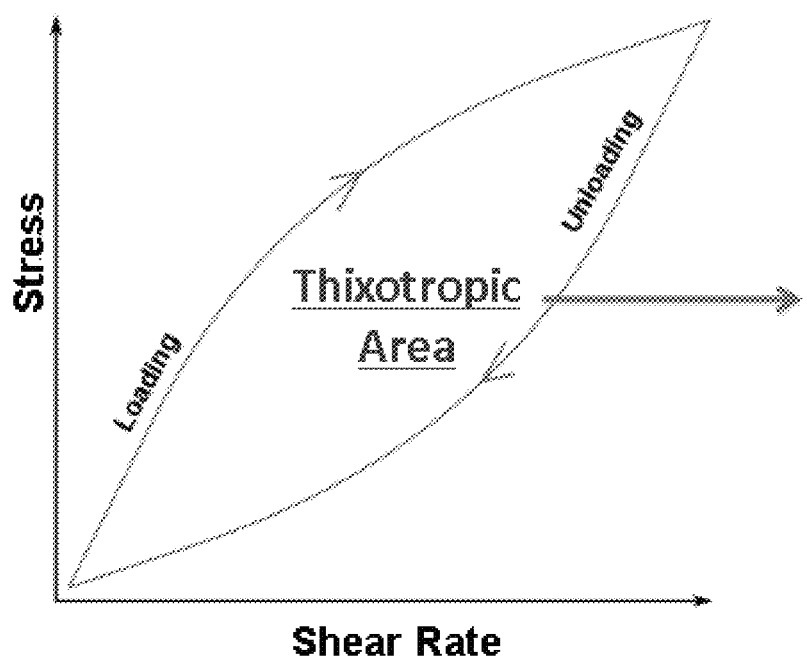
FIG. 16A is an example graph showing the analysis that is used to determine if shear-thinning is time dependent. A shear thinning material that exhibits a time dependent viscosity build after shearing is termed thixotropic. Following a period of shearing, some materials will very quickly recover their viscosity whereas others will take hours
Figure 16B:
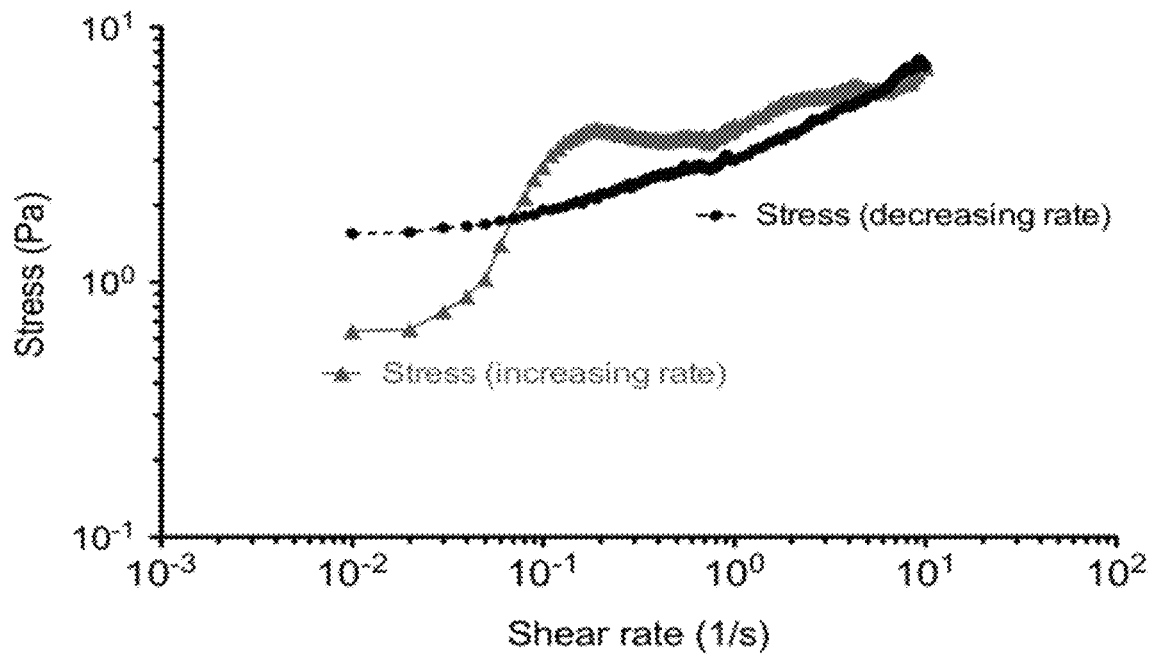
FIG. 16B is a graph showing studies to assess possible time dependent shear-thinning in the Wharton's Jelly compositions. The sample is subjected to increasing shear and then reducing shear. The results give an indication whether the sample is thixotropic. A thixotropic material will behave differently on the way up and down. Results of the studies shown in the graph demonstrate that Wharton's Jelly compositions produced by the methods disclosed herein do act as thixotropic materials. One important thixotropic materials is that they are often highly effective as injectable compositions.

A shear thinning material that exhibits a time dependent viscosity build after shearing is termed thixotropic. Following a period of shearing, some materials will very quickly recover their viscosity whereas others will take hours. FIG. 16A is an example graph showing the analysis that is used to determine if shear-thinning is time dependent (i.e., if material is thixotropic). The sample is subjected to increasing shear and then reducing shear. The results give an indication whether the sample is thixotropic. Specifically, a thixotropic material will behave differently on the way up and down. FIG. 16B is a graph showing studies to assess possible time dependent shear-thinning in the Wharton's Jelly compositions. Results of the studies shown in the graph demonstrate that Wharton's Jelly compositions produced by the methods disclosed herein do act as thixotropic materials. One important property of thixotropic materials is that they are often highly effective as injectable compositions.

It should be observed that while the foregoing detailed description of various embodiments of the present invention is set forth in some detail, the invention is not limited to those details and devices, kits and methods according to the invention can differ from the disclosed embodiments in numerous ways. It will be appreciated that the functions disclosed herein as being performed by particular embodiments may be performed differently in an alternative embodiment. It should be further noted that functional distinctions are made above for purposes of explanation and clarity; structural distinctions in a system or method according to the invention may not be drawn along the same boundaries. Hence, the appropriate scope hereof is deemed to be in accordance with the claims as set forth below.

REFERENCES

The following references, to the extent that they provide exemplary procedural or other details supplementary to those set forth herein, are specifically incorporated herein by reference.

U.S. Pat. Nos. 5,919,702; 8,900,863; and 9,012,222
United States Patent Publication 2008/0118477
United States Patent Publication 2011/0151556
United States Patent Publication 20130072951
United States Patent Publication 2013/0183273
United States Patent Publication 20140120615
PCT Publication WO/2008/060037A1
PCT Publication WO/2011/101834
Stem Cell Res Ther. 2015 Mar. 19; 6:38. doi: 10.1186/s13287-015-0031-3.
PLoS One. 2014 Oct. 20; 9(10):e110764. doi: 10.1371/journal.pone.0110764. eCollection 2014.
Stem Cell Res Ther. 2014 May 2; 5(3):62. doi: 10.1186/scrt451.
Int J Mol Sci. 2013 May 31; 14(6):11692-712. doi: 10.3390/ijms140611692.
Int Rev Neurobiol. 2013; 108:79-120. doi: 10.1016/B978-0-12-410499-0.00004-6.
Neural Regen Res. 2013 Jul. 5; 8(19): 1783-1792.
Placenta. 2011 October; 32 Suppl 4:S311-5. doi: 10.1016/j.placenta.2011.06.010. Epub 2011 Jul. 6.
Tissue Engineering Part A (Impact Factor: 4.64). June 2011; 17(21-22):2651-61. DOI: 10.1089/ten.TEA.2010.0587.
Stem Cell Rev. 2010 March; 6(1):15-26. doi: 10.1007/s12015-009-9102-0.
Tissue Eng Part A. 2009 September; 15(9):2325-34. doi: 10.1089/ten.tea.2008.0402.
Haematologica. 2006 August; 91(8):1017-26. Epub 2006 Jul. 25.

What is claimed is:

1. An apparatus for processing an umbilical cord, the apparatus comprising:
a clamping mechanism configured to clamp an umbilical cord;
an extraction mechanism, wherein the extraction mechanism is configured to:
engage the umbilical cord;
translate along the umbilical cord;
increase hydrostatic pressure within the umbilical cord; and
extract matter from the umbilical cord; and
a receptacle configured to retain the matter extracted from the umbilical cord, wherein the receptacle comprises:
a plurality of openings sized to prevent an egress of substantia gelatinea Juniculi umbilicalis (Wharton's Jelly) stored within the receptacle.

2. The apparatus of claim 1, wherein the extraction mechanism is configured to extract substantia gelatinea faniculi umbilicalis (Wharton's Jelly) from the umbilical cord.

3. The apparatus of claim 1, wherein the extraction mechanism comprises rollers configured to compress the umbilical cord.

4. The apparatus of claim 1, wherein the extraction mechanism comprises a first housing and a second housing configured to couple together.

5. The apparatus of claim 1, wherein the extraction mechanism comprises:
a first end;
a second end; and
a plurality of rollers between the first end and the second end.

6. The apparatus of claim 5, wherein:
the plurality of rollers comprises a first pair of corresponding rollers proximal to the first end of the extraction mechanism;
the plurality of rollers comprises a second pair of corresponding rollers proximal to the second end of the extraction mechanism;
the first pair of corresponding rollers are spaced a first distance apart;
the second pair of corresponding rollers are spaced a second distance apart;
and the first distance is greater than the second distance.

7. The apparatus of claim 6, further comprising a third pair of corresponding rollers between the first and second pairs of corresponding rollers, wherein:
the third pair of corresponding rollers are spaced a third distance apart; and
the third distance is greater than the first distance and less than the second distance.

8. The apparatus of claim 1, wherein the clamping mechanism comprises a plurality of protrusions configured to grip the umbilical cord.

9. The apparatus of claim 1, wherein:
the clamping mechanism comprises a first housing and a second housing; and
the first housing and the second housing are configured to couple together around the umbilical cord.

10. The apparatus of claim 1, wherein the receptacle comprises:
a first opening configured to receive matter extracted from the umbilical cord;
and a cover configured to be placed over the first opening.

11. The apparatus of claim 1, wherein the receptacle comprises a removable sheath.

* * * * *